United States Patent [19]

Navia et al.

[11] Patent Number: 5,498,709
[45] Date of Patent: Mar. 12, 1996

[54] PRODUCTION OF SUCRALOSE WITHOUT INTERMEDIATE ISOLATION OF CRYSTALLINE SUCRALOSE-6-ESTER

[75] Inventors: Juan L. Navia, Athens; Robert E. Walkup; Nicholas M. Vernon, both of Watkinsville; David S. Neiditch, Athens, all of Ga.

[73] Assignee: McNeil-PPC, Inc., Milltown, N.J.

[21] Appl. No.: 448,710

[22] Filed: May 24, 1995

Related U.S. Application Data

[63] Continuation-in-part of Ser. No. 323,954, Oct. 17, 1994, abandoned.

[51] Int. Cl.$^6$ .................. C07G 17/00; C07H 1/00; C07H 3/00
[52] U.S. Cl. .................. 536/124; 536/4.1; 536/127; 536/119; 127/46.3
[58] Field of Search .................. 536/4.1, 124, 127, 536/119; 127/46.3

[56] References Cited

U.S. PATENT DOCUMENTS

| | | | |
|---|---|---|---|
| 4,380,476 | 4/1983 | Mufti et al. | 127/46.3 |
| 4,918,182 | 4/1990 | Jackson et al. | 536/124 |
| 4,950,746 | 8/1990 | Navia | 536/124 |
| 4,980,463 | 12/1990 | Walkup et al. | 536/4.1 |
| 5,023,329 | 6/1991 | Neiditch et al. | 536/124 |
| 5,034,551 | 7/1991 | Vernon et al. | 536/119 |
| 5,089,608 | 2/1992 | Walkup et al. | 536/124 |
| 5,128,248 | 7/1992 | Dordick et al | 536/124 |
| 5,136,031 | 8/1992 | Khan et al. | 536/4.1 |
| 5,298,611 | 3/1994 | Navia et al. | 536/4.1 |

Primary Examiner—Ronald W. Griffin
Attorney, Agent, or Firm—Charles J. Metz

[57] ABSTRACT

There is disclosed a process for producing sucralose from sucralose-6-ester whereby the sucralose-6-ester is deacylated directly either prior to or after removal of the tertiary amide reaction vehicle from the neutralized chlorination reaction mixture, to produce an aqueous solution of sucralose plus salts and impurities, from which sucralose is recovered by extraction and is then preferably purified by crystallization.

15 Claims, No Drawings

PRODUCTION OF SUCRALOSE WITHOUT INTERMEDIATE ISOLATION OF CRYSTALLINE SUCRALOSE-6-ESTER

CROSS-REFERENCE TO RELATED APPLICATIONS

This application is a continuation-in-part of application Ser. No. 08/323,954, filed Oct. 17, 1994, now abandoned.

The invention relates to a process for the production of sucralose without intermediate isolation of sucralose-6-ester.

BACKGROUND OF THE INVENTION

The artificial sweetener 4,1',6'-trichloro-4,1',6'-trideoxygalactosucrose ("sucralose") is derived from sucrose by replacing the hydroxyls in the 4, 1' and 6' positions with chlorine. In the process of making the compound, the stereo configuration at the 4 position is reversed. Therefore, sucralose is a galacto-sucrose having the following molecular structure:

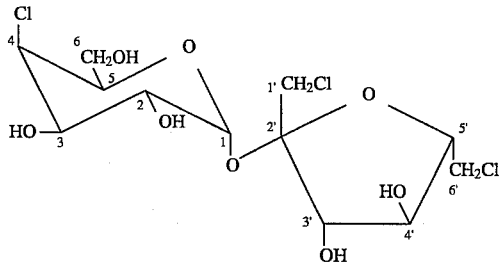

The direction of the chlorine atoms to only the desired positions is a major synthesis problem because the hydroxyls that are replaced are of differing reactivity; two are primary and one is secondary. The synthesis is further complicated by the fact that the primary hydroxyl in the 6 position is unsubstituted in the final product.

A number of different synthetic routes for the preparation of sucralose have been developed in which the reactive hydroxyl in the 6 position is first blocked, as by an ester group, prior to the chlorination of the hydroxyls in the 4, 1' and 6' positions, followed by hydrolysis to remove the ester substituent to produce sucralose. Several of such synthesis routes involve tin-mediated syntheses of sucrose-6-esters. Illustrative are the tin-mediated routes disclosed by Navia (U.S. Pat. No. 4,950,746), Neiditch et al. (U.S. Pat. No. 5,023,329), Walkup et al. (U.S. Pat. No. 5,089,608- "Walkup et al.-I"), Vernon et al. (U.S. Pat. No. 5,034,551), and Sankey et al., U.S. patent application Ser. No. 08/237,947, filed May 2, 1994, and assigned to the same assignee as this application.

The sucrose-6-esters produced by the above-cited synthesis routes are typically chlorinated by the process of Walkup et al., U.S. Pat. No. 4,980,463 ("Walkup et al.-II"). The chlorination process produces as a product a sucralose-6-ester, such as 4,1',6'-trichloro-4,1',6'-trideoxygalactosucrose-6-acetate ("TGS-6-Ac", when the sucralose-6-ester is the acetate ester, or, more generally, "TGS-6-ester") in solution in a tertiary amide, typically N,N-dimethylformamide ("DMF"), plus salts (produced as a result of neutralizing the chlorinating agent after completion of the chlorination reaction), and impurities. In one aspect, the present invention provides a process for the recovery of the TGS-6-ester from the solution in tertiary amide that is the product of the chlorination process of Walkup et al.-II.

In previous processes that have been disclosed, such as the processes disclosed in Walkup et al.-II and the process disclosed in Navia et al., "RECOVERY OF SUCRALOSE INTERMEDIATES", U.S. patent application Ser. No. 08/198,744, filed Feb. 18, 1994 (and re-filed on Jan. 1, 1995, as U.S. patent application Ser. No. 08/368,466), and assigned to the same assignee as this application, sucralose is produced from the chlorination reaction mixture of Walkup et al.-II by the following procedure:

a. after the neutralization step, the tertiary amide reaction vehicle for the chlorination reaction is removed, as by steam distillation (disclosed in Navia et al.), which forms an aqueous mixture containing salts, TGS-6-ester and impurities;

b. the TGS-6-ester is then recovered from the aqueous mixture by extraction using a suitable organic solvent, such as ethyl acetate;

c. the crude TGS-6-ester is then de-acylated to form sucralose; and d. the sucralose is recovered by counter-current extraction and purified by crystallization.

The present invention provides a process whereby the TGS-6-ester is de-acylated directly, to produce an aqueous solution of sucralose plus salts and impurities, from which sucralose is recovered, as by extracting with an organic solvent, and preferably the sucralose is then purified by counter-current extraction, crystallization or a combination of both techniques.

The process of this invention has several potential economic advantages over sucralose processes described before, e.g., the process disclosed in Navia et al., Ser. No. 08/368,466. These include the following:

1. Reduction of solids handling steps in the overall process, in that TGS-6-Ac is not discretely isolated. This effectively reduces the equipment needed (e.g., less need for centrifuges used for separation of solids from liquids);

2. Probable reduction in the need to re-crop mother liquors (i.e., fewer re-crystallization steps). This is because crystallization of sucralose seems to be easier than crystallization of sucralose-6-acetate; and 3. Overall yields appear to be increased slightly. This may be due to the conversion of diacetates that have the correct chlorination substitution to sucralose. These diacetates would be lost in the Navia et al. process because of the rigorous purification of TGS-6-Ac in Navia et al.

BRIEF DESCRIPTION OF THE INVENTION

The invention provides a process for producing sucralose from a feed mixture of (a) 6-O-acyl-4,1',6'-trichloro-4,1',6'-trideoxygalactosucrose ["TGS-6-ester"], (b) salt including alkali metal or alkaline earth metal chloride, (c) water, and (d) other chlorinated sucrose by-products, in a reaction medium comprising a tertiary amide, wherein said process comprises:

(i) deacylating the 6-O-acyl-4,1',6'-trichloro-4,1',6'-trideoxygalactosucrose, to produce an aqueous solution comprising sucralose, (b) salt including alkali metal or alkaline earth metal chloride, and (d) other chlorinated sucrose by-products; and (ii) recovering sucralose from the product of step (i), as by extraction followed by crystallization or by extractive techniques alone.

DETAILED DESCRIPTION OF THE INVENTION

In one aspect, the invention provides a process for producing sucralose from a feed mixture of (a) 6-O-acyl-4,1', 6'-trichloro- 4,1',6'-trideoxygalactosucrose, (b) salt including alkali metal or alkaline earth metal chloride, (c) water, and (d) other chlorinated sucrose by-products, in a reaction medium comprising a tertiary amide, wherein said process comprises:

(i) deacylating the 6-O-acyl-4,1',6'-trichloro-4,1',6'-trideoxygalactosucrose, as by raising the pH of the aqueous solution of (a), (b), (c) and (d) to about 11 (±1) at a temperature and for a period of time sufficient to effect said deacylation, to produce an aqueous solution comprising sucralose, salt including alkali metal or alkaline earth metal chloride, and other chlorinated sucrose by-products, in a reaction medium comprising a tertiary amide;

(ii) removing said tertiary amide, as by steam distillation or by extraction; and (iii) recovering sucralose from the product of step (ii), as by extraction followed by crystallization, or by extractive techniques alone.

In another aspect, the process of the invention is carried out by removing the tertiary amide prior to deacetylation, for instance, by the following steps:

(i) removing said tertiary amide, as by steam distillation, to produce an aqueous solution of (a), (b) and (d) from which a major proportion of the tertiary amide in said feed mixture has been removed;

(ii) deacylating the 6-O-acyl-4,1',6'-trichloro-4,1',6'-trideoxygalactosucrose, as by raising the pH of the aqueous solution product of step (i) to a pH of about 11 (±1) at a temperature and for a period of time sufficient to effect said deacylation, to produce an aqueous solution comprising sucralose, salt including alkali metal or alkaline earth metal chloride, and other chlorinated sucrose by-products; and (iii) recovering sucralose from the product of step (ii), as by extraction followed by crystallization or by extractive techniques alone.

The process of the invention employs as its feed mixture a composition comprising 6-O-acyl-4,1',6'-trichloro-4,1',6'-trideoxygalactosucrose in a tertiary amide (preferably DMF) reaction medium, such as the neutralized (quenched) product of the chlorination reaction described by Walkup et al.-II, cited above. The preferred 6-O-acyl-4,1',6'-trichloro-4,1',6'-trideoxygalactosucrose esters are 6-O-acetyl-4,1',6'-trichloro-4,1',6'-trideoxygalactosucrose and 6-O-benzoyl-4,1',6'-trichloro-4,1',6'-trideoxygalactosucrose.

On the laboratory scale, the crude chlorination product may be quenched in a batch operation by the addition (in one portion) of one molar equivalent (basis phosgene) of ice-cold aqueous solutions or slurries of the alkali or alkaline earth metal hydroxides following the teachings of Walkup et al.-II. Preferred alkaline agents include the hydroxides of sodium, potassium, and calcium. More dilute aqueous alkaline solutions, such as for example 3 to 4N sodium hydroxide, are preferred. Broader ranges of concentration can be used (such as, for example, 2 to 8N sodium hydroxide). At the lower concentrations, precipitation of salts is reduced or avoided, which significantly reduces the amount of solids the process stream must accommodate. However, when the concentration becomes too low (e.g., below about 2N), the product stream becomes diluted to an extent that may adversely affect the efficiency of the process.

In a preferred method of practice of this quench method, cold aqueous alkali is added with vigorous stirring as rapidly as possible in a quantity sufficient to raise the pH to 8–10. After stirring several minutes at this mildly elevated pH, the quenched solution is neutralized to pH 5–7 by the addition of an acid, such as, for example, concentrated aqueous hydrochloric acid or glacial acetic acid. The brief treatment of the quenched chlorination reaction mixture at pH 8–10 has the beneficial effect of insuring that all of the hydroxyl groups of the sucrose-6-ester that have not been replaced by chlorine atoms are returned to their original hydroxyl group form.

Alternatively, one can add sufficient aqueous alkali to attain a pH of 11 (±1) and hold for sufficient time to remove the 6-acyl function and obtain sucralose directly, in the presence of all the salts, residual tertiary amide (DMF), etc. This is carried out at the expense of some DMF which is lost by caustic hydrolysis to dimethylamine and sodium formate. For this reason, and as is explained in more detail below, the deacylation prior to removal of DMF is less preferred, since it is desired to recover all the DMF for recycle and re-use.

The batch method for quenching the crude chlorination product mixture suffers from scale limitations owing to inefficiencies in heat and mass transport. An improved method, known as the "dualstream" or "concurrent addition" method, involves mixing streams of aqueous alkali and cooled (to about room temperature) crude chlorination product together at carefully metered rates with vigorous agitation under conditions of pH and temperature control. The primary advantages of the dual-stream quench method are that it provides for complete control of pH, temperature, and rate of mixing throughout the course of the quench. Thus, side reactions resulting in product losses are minimized. A further advantage of the dual-stream quench method is that it may be operated continuously by using a quench vessel fitted with either a bottom drain or a pump. By operating the dual-stream quench method in a continuous mode, a relatively large amount of crude chlorination product can be processed using a quench vessel of modest size. This continuous operation is a rough approximation of an in-line mixing process that might be employed for quenching in a commercial operation.

Using a 1500-ml jacketed quench vessel, it was determined that crude sucralose-6-ester product mixtures can be quenched efficiently using a chlorination mixture constant feed rate of about 10 ml per minute, a quench mixture temperature of about 15° C. (coolant temperature 5° C.), a four-bladed propeller-type stirrer 24 with a stirring rate sufficient to insure good mixing, and a pH control setting of pH 8.5 on the pH control pump. These results were obtained with 3N or 4N NaOH as the alkaline agent, and with a starting charge of about 100 ml of between 3:1 to 1:3 DMF-$H_2O$ in the quench vessel (in order to have sufficient solution volume for accurate pH measurement during the early stages of the quench).

DMF REMOVAL

When sodium hydroxide is used in the quench step and the tertiary amide is DMF, the salts that are formed in the quench step include sodium chloride, dimethylamine hydrochloride and small amounts of sodium formate. If the quench were to be continued with a deacylation by increasing the pH sufficient to effect deacylation, the extraction of sucralose from the quenched and thus deacylated product mixture would be complicated by the presence of DMF (or other tertiary amide) and its propensity to distribute between both organic and aqueous phases in the extraction step, which would be the logical next step in a process sequence for producing sucralose. The tertiary amide would dissolve sucralose in both phases, and would also tend to dissolve other materials present in both phases, which would make recovery of the sucralose in good yield difficult and/or expensive. Also, the presence of DMF or other tertiary amide interferes with the efficiency of the purification of sucralose by crystallization from the extraction solvent. A further probable complication would be the base-catalyzed decomposition of the tertiary amide. For all of these reasons, the tertiary amide such as DMF should be removed prior to recovery and purification of the sucralose. Further, it is preferred to remove the DMF prior to the deacylation step.

The steam stripping operation is carried out so as to remove a major proportion of the DMF (or other tertiary amide) in the quenched feed mixture (preferred mode) or in the quenched and deacylated reaction mixture. It is desired to remove at least 95%, and preferably, from about 98 to 99.9%, of the DMF in order to avoid the undesirable consequences outlined in the previous paragraph.

Upon removal of the DMF (or other tertiary amide) by steam stripping, the DMF is effectively replaced with water in the process stream and the DMF can subsequently be recovered from the aqueous overheads by distillation and can be recycled.

An example of a laboratory-scale falling-film packed-column steam distillation apparatus designed for stripping the DMF from quenched sucralose-6-ester chlorination products is a 5.0-cm diameter, 90-cm long vacuum-jacketed distillation column packed with 5-mm Raschig rings or other suitable packing. Alternatively, a 15-plate, jacketed, Oldershaw column can be used. The quenched product, which is typically preheated, is introduced into the top of the column at a rate of about 5.0–5.5 grams per minute. Steam is introduced into the column through a sidearm located at the bottom of the column. As condensate-free steam is required, the steam is passed through a "preboiler" to trap any condensate carried over. In the laboratory, this preboiler is typically a small multineck flask fitted with a heating mantle. Typical steam feed rates are in the range of 38–47 grams per minute (calculated by adding the weights of overhead and bottom products, and then subtracting the weight of chlorination feed), which corresponds to a steam-to-feed ratio ranging from 4:1 to 12:1, with steam to feed ratios of between 7.5:1 and 9:1 being typical for the packed column assembly. The preferred embodiment would use more plates with a lower steam:feed ratio, e.g., 15 plates with a steam/feed ratio of about 4:1.

The preheating of the quenched chlorination feed before it is introduced onto the top of the column is conducted in order to increase the efficiency of the stripping operation. Preheating is typically conducted in the laboratory by passing the feed through an enclosed glass coil apparatus heated with a secondary source of steam. The feed is normally heated to about 90°–95° C. The efficiency of DMF removal can also be enhanced by employing a "reboiler" (i.e., by heating the bottoms product in such a way that it refluxes up into the stripping column).

Temperatures are advantageously measured at two places on the apparatus using thermocouple devices. In addition to the quenched chlorination feed temperature described above, the temperature of the vapors passing through the distillation column head are also measured. Head vapor temperatures are typically in the range of from about 99° C. to about 104°C.

A typical quenched chlorination product of sucrose-6-acetate contains about 1.5–5 wt % sucralose-6-ester, about 35–45 wt % DMF, about 35–45 wt % water, and about 12–18 wt % salts. After passage of such product mixture through the laboratory-scale steamstripping apparatus, bottoms products will typically consist of about 1–3 wt % sucralose-6-ester, about 0.1–0.5 wt % DMF, about 80–90 wt % water, and about 8–12 wt % salts (expressed as NaCl, based on sodium and chloride assays).

Under typical laboratory conditions, which involve a column residence time of 7–10 minutes, no decomposition of sucralose-6acetate is detectable, provided the pH of the quenched chlorination feed is neutral to slightly acidic (pH 5.0–7.0).

Similar conditions can be used for steam-stripping the DMF from a quenched and deacylated reaction mixture.

SUCRALOSE-6-ESTER DEACYLATION

In the preferred mode of the invention, following removal of the tertiary amide, the sucralose-6-ester is deacylated by increasing the pH of the reaction mixture to about 11 ($\pm 1$) at a temperature and for a period of time sufficient to effect the deacylation. This step is typically carried by adding sufficient alkali metal hydroxide, such as sodium hydroxide, with agitation, to increase the pH to the desired level. Reaction times and temperatures within the range of about 30 minutes to 2 hours at 15°–35° C. have been found to be useful. At the conclusion of the deacylation, the base present will normally be neutralized, as by addition of hydrochloric acid, to a pH of about 5 to 7. After the neutralization, the aqueous reaction mixture contains sucralose, salts (as above, plus the salt produced by the neutralization step described immediately above), and other chlorinated sucrose byproducts.

SUCRALOSE EXTRACTION

Following the deacylation, sucralose may be isolated by extraction of the aqueous brine solution with a variety of organic solvents. These solvents include methyl acetate, ethyl acetate, methyl ethyl ketone, methyl iso-butyl ketone, methyl iso-amyl ketone, methylene chloride, chloroform, diethyl ether, methyl tert-butyl ether, and the like. A preferred solvent, for reasons of extraction selectivity, ease of recycle, and toxicological safety, is ethyl acetate.

Sucralose isolation is typically conducted in the laboratory by first partially evaporating the crude neutralized deacylation reaction product. About half the water present may optionally be removed, producing a solution containing about 2–5 wt % carbohydrates and about 15–25 wt % salts. Isolation is normally conducted by carrying out three sequential extractions with ethyl acetate or other appropriate solvent. The extracts are combined, and may optionally be washed with water (to partially remove any residual DMF and dichlorodideoxysucrose derivatives which to some extent are partitioned into the organic phase).

In addition to the batch extraction technique outlined above, extraction may also be carried out continuously on the dilute (not concentrated by evaporation) stream in a counter current mixersettler extraction system. The advantage is that no prior evaporation-concentration step is required. Such counter-current extraction techniques are known in the art.

Once the crude sucralose has been recovered from the aqueous brine as a solution in an appropriate organic solvent, it is concentrated and the product can be purified by crystallization and recrystallization from the same solvent until the required purity is achieved. Alternatively, the sucralose may be crystallized from a solvent mixture such as methanol-ethyl acetate or from water to achieve the desired purity level. Sequential partitioning of the sucralose between solvent-water mixtures in a counter-current manner also allows a purification to be achieved and likewise opens the possibility of a direct liquid fill process (i.e., no material isolation needed; the final process stream having the requisite specifications to be directly packaged for use).

Another noteworthy aspect of the purification/recovery process described above (that is, extraction followed by crystallization) is that the same solvent can be used for extraction and the purification step. Typically (i.e., with other chemical materials), it is rare that the chemical product to be purified will crystallize from the same solvent that is used to extract it. In the present case, however, a combination of dilution and relatively low levels of impurities allows the sucralose to remain in solution during the extraction, and then after the solution containing the extracted sucralose is concentrated, the sucralose product can then be crystallized from the same solvent.

EXPERIMENTAL

Chlorination of Sucrose-6-Acetate

A solution of crude sucrose-6-acetate in DMF (1.447 Kg) containing 416.94 g (1.084 moles) sucrose-6-acetate was diluted with 2.51 kg fresh DMF. The solution was cooled to −2° C (dry ice/acetone/water bath) and stirred vigorously while phosgene (1.125 Kg, 99%, 11.26 moles) was added at a rate of 5.4 to 6.7 g/min. The temperature of the mixture was kept at 5°–12° C. during most of the addition.

The reaction mixture was allowed to stir at ambient temperature for 30 minutes, then heated to 115° C. over a 2–3 hour period, then held at 115° ±1° for 1.75 hrs, then cooled to 35° C. over 30 min. The final mass, 4.34 kg, was carried on to the dual stream caustic quench and further processing.

DUAL STREAM QUENCH

The chlorinated mixture (typically about 3.5–4.5 kg) was pumped with an FMI Lab pump (model RP-G20) at 10 ml/min into a jacketed, 2-L resin kettle (without the top) with stopcock at the bottom, containing 200 ml of 1:1 mixture of DMF-water. Aqueous NaOH (3N, 12%) 5 kg, was delivered at the same time by a pH controlled prominent pump with the pH set point at 9.0 and pump stroke set to 25%. The proportional bandwidth was at the maximum setting (±1 pH unit) to minimize any overshoot of pH. The jacket temperature of the quench flask was controlled with Forma Scientific circulating bath. The jacket temperature was maintained at 5° C. The temperature of the quench mixture was initially at 6° C and rose to 20° C. in the first 10 minutes. Thereafter, the temperature stabilized at about 17° C. over the entire period of quench. During the quench, pH fluctuated between 8.0 to 8.5 in the flask. The mixture was vigorously agitated with a heavy-duty laboratory stirrer. The quenched mixture was removed from the vessel in portions as the quench vessel filled to capacity. Each batch was quenched in approximately 6 hours at the above conditions. For most batches, approximately 9 kg of quenched mixture were obtained. 4,1',6'-Trichloro-4,1',6'-trideoxygalactosucrose-6-acetate ("TGS-6Ac") was present at 2%-wt in the mixture. The conditions and parameters were optimized to achieve less than 2 mole-percent deacetylation during quenching.

All the quenched batches were vacuum filtered to remove insoluble particulate matter using either vacuum filtration through a sintered glass Buchner funnel or centrifugation. The filtrate was sampled for analysis and carried on to steam stripping.

STEAM STRIPPING

1. Laboratory Scale:

The quenched mixtures were steam stripped in batches. Two things were accomplished via steam stripping—1) removal of DMF to ease extraction, 2) removal of tarry, polymeric soluble material found in quenched mixtures. The steam stripping was carried out in a well insulated 4 foot tall glass column with an I.D. of 4 inches. The conditions were optimized to obtain less than 1% DMF in the bottoms. The column was packed with ¼" size Raschig rings. The steam to feed ratio was maintained in the range of 6 to 8. After every three batches steam stripped, the column was cleaned with 1N caustic solution, which removes the tarry, polymeric materials from the packing and column surfaces. A typical run of steam stripping was completed in 6 hours time. For every 9 kg batch of feed, approximately 13 kg of steam-stripped bottoms were produced with a TGS-6-Ac concentration of about 1.5%-wt.

The usual method of operation was to pump the quenched, filtered mixture with an FMI Lab pump (RP-G20) through a preheater, consisting of a 4" Graham-type condenser with steam in the jacket, then directly into the center of the top of the column. Steam was passed through a reboiler (a 3-neck, 500 ml flask with a magnehelic low pressure gauge, and a heating mantel) to remove condensate before entering the column at the bottom below the packing. Column pressure remained at 0–3 in. of water throughout the operation. Feed rate was determined initially by timing the pumping rate from a graduated reservoir. The bottoms collection rate was measured by collecting in a graduated receiver. The distillation rate was measured, by condensing the effluent from the top of the column, as ml/min. The steam rate was determined by difference (STEAM=TOPS+BOTTOMS−FEED).

2. Larger Scale Steam Stripping:

Chlorinated and quenched process streams, of composition similar to preceding laboratory scale examples, were fed above the top tray of a 10 inch diameter column containing 20 sieve trays while steam was directed into the bottom of the column. A steam/feed ratio of approximately 3 was maintained to achieve the desired removal of DMF in the bottoms stream (>99.2% removal based on assayed amount of DMF charged to the column in the feed). Pre-heating the feed stream to 80–90° C. was beneficial in improving the stripping efficiency in the column. The DMF/Water stream is stripped overhead by the counter-current steam flow. The column bottoms containing the TGS-6-Ac, salts and water was delivered to the next process area for purification. The overheads are sent to another column for DMF recovery (typical composition 12% DMF, 88% water). In this manner, quenched feed containing 1.8% TGS-6-Ac, 8.5% salts, 54.6% water, and 30.4% DMF, was stripped to produce bottoms containing 1.6% TGS-6-Ac, 9.8% salts, 84.9% water, and 0.1% DMF residual (99.6% removal of DMF). The ratio of steam strip feed mass to bottoms mass was about 1.22.

DEACETYLATION OF STEAM-STRIP BOTTOMS

The crude brine solution of TGS-6-Ac (15.4 kg.) obtained after removal of DMF by steam distillation, similar to the procedure described above, was subjected to deacetylation by raising the pH of the solution to 11.5. This was accomplished by adding 50% w/w sodium hydroxide to the rapidly stirred solution using a metering pump under pH control. Sufficient caustic was added to the solution to raise the pH to 11.5 and maintain it at that level for about 2 hours at ambient temperature. When the deacetylation was deemed complete, the solution was neutralized with concentrated hydrochloric acid.

ISOLATION OF SUCRALOSE FROM THE DEACETYLATED MIXTURE

The crude deacetylated mixture was extracted continuously with ethyl acetate using a ROBATEL counter-current extractor. The aqueous phase (feed) and ethyl acetate (extractant) were delivered to the ROBATEL by two Masterflex Digistat peristaltic pumps in the proportion of 4:1 (extractant:feed).

The ethyl acetate solution containing the desired product was evaporated to a thick syrup which was dissolved in water. This aqueous solution was treated with decolorizing carbon, then evaporated again to a thick syrup. The syrup was diluted with fresh ethyl acetate. The solution was seeded with sucralose crystals and allowed to stand and crystallize at ambient temperature over several days. Sucralose was obtained as a white crystalline solid (24 g; 92.7% w/w). Additional crops were obtained by repeatedly evaporating the solvent and redissolving the syrup in fresh ethyl acetate. In all, 33.5 g (40.6%) of the sucralose was recovered as solid product with a similar purity as before. The remainder in the mother liquor continued to crystallize out more slowly over several days. Additional material may be obtained in subsequent crops or by recycle of the mother liquor into subsequent crystallizations.

Isolation of Crystalline Sucralose from Water.

An ethyl acetate solution obtained as described previously was concentrated to a thick, dark syrup (62 g, 95–97% sucralose). The syrup was diluted with sufficient water to make a 20% sucralose solution, the solution was treated with 5 g decolorizing carbon, and filtered to give a light straw colored solution. The solution was concentrated to about 65% sucralose, cooled to ambient temperature, seeded with sucralose crystals, and allowed to crystallize while stirring over 5 days. The crystalline slurry was concentrated slightly by vacuum distillation of water to about 70–75% sucralose and the crystallization continued a further 24 hours. The crystalline product was recovered by filtration and air dried to give 20.2 g of product.

CHLORINATION WITH ARNOLD'S REAGENT/PREPARATION OF SUCRALOSE

Sucrose-6-acetate (18.93 g) and DMF (172 g) were charged into a 500 mL, 4-neck round bottomed flask equipped with an overhead stirrer, thermometer, and vacuum distillation set-up. The mixture was vacuum distilled until about 50 mL of distillate was collected (54.8 g lost) [This is a drying step to remove residual moisture].

The residue was cooled to 0–5° C., the distillation apparatus was replaced with a water condenser and drying tube, and chloromethylenedimethylammonium chloride (Arnold's Reagent; 46.8 g, 347.34 mmol) was added in large portions while keeping the internal reaction temperature below 30° C. The mixture was then heated to 65° C. over 20 minutes, held at this temperature for 5 minutes, heated to 110–115° C. over 25 minutes and held within that range for 3.75 hours. The reaction mixture was then cooled to 0–5° C. and made basic by the addition of 189g of 3 molal aqueous sodium hydroxide solution which had been pre-cooled to 0° C. After 45 minutes the deacylation to crude sucralose was complete (monitored by TLC), and the mixture was neutralized by the addition of 17.8 g of glacial acetic acid. HPLC assay of the crude mixture indicated that the mixture contained 11.35 g (65% yield) of sucralose.

Steam stripping was performed to remove the DMF according to previously described procedures. Results from Arnold's chlorinations and chlorinations conducted by the direct introduction of phosgene to DMF solutions of sucrose-6-acetate indicate that between 80–90% of the theoretical amount of DMF can be recovered.

The crude sucralose product is recovered from the DMF depleted stripper bottoms by extraction with an appropriate aqueous brine-immiscible organic solvent [examples include dichloromethane, chloroform, 2-butanone, cyclohexanone, ethyl acetate; with the latter two being particularly effective and desirable for process and toxicological reasons]. The aqueous organic extracts were back-extracted with water to transfer the sucralose to the aqueous phase. The water solution was decolorized with carbon, concentrated, and the sucralose crystallized in >91% w/w purity on a carbohydrate basis. The mother liquors may be used for recycle to obtain additional material. Alternatively, the sucralose may be purified by a prior crystallization from the organic extraction medium (particularly ethyl acetate), which will facilitate separation of the desired product from less polar materials and color-bodies.

The following example demonstrates the use of the sucrose-6-benzoate analogue to perform the same transformation, i.e., debenzoylation immediately subsequent to the chlorination step to generate crude sucralose. In this case, the DMF was not removed by steam stripping, and the extractive purification approach was employed. This aspect of the invention (i.e., the extractive purification approach vs. steam distillation of the DMF), while operative, is not preferred because the DMF reduces the yield by interfering with the recovery of the crude sucralose, e.g., residual DMF, which is carried through the extractions, interferes with the crystallization of sucralose.

CHLORINATION OF SUCROSE-6-BENZOATE DIRECT CONVERSION TO CRUDE SUCRALOSE

To a 100 mL, 3-necked round bottomed flask, equipped with magnetic stirring, thermometer, addition funnel, air-cooled condenser, and argon inlet was charged 18 mL of DMF. This was cooled to −5° C., and to it was added 6.8 mL (99% pure; 71.7 mmol) of phosphorus oxychloride dropwise at such a rate as to maintain the internal temperature at or below 10° C. After completion of this addition, the mixture was cooled to −10° C., and to it was added dropwise a solution consisting of 5.0 g (91.2% pure; 10.21 mmol) dissolved in 9 mL of dry DMF at such a rate as to ensure that the internal temperature did not exceed 6° C. After completion of this addition, the clear reaction mixture was warmed to 60° C. over 20 minutes. The heating was then increased over a 15 minute period to attain an internal temperature of 85° C., at which temperature the mixture was maintained for 1 hour. The resulting golden-yellow solution was then heated to 115° C. and maintained there for 3 hours. The resulting red-brown mixture was then cooled to ca. 50° C., and to it was added in a single portion, 145 mL of 4N aqueous sodium hydroxide (580 mmol) which had been pre-cooled, along with 35 g of ice. The alkaline mixture was stirred at ambient temperature for 45 minutes whereafter TLC analysis indicated that the conversion of sucralose-6-benzoate to sucralose was complete. The mixture was extracted twice with 150 mL each toluene to remove non-polar impurities, and was thereafter repeatedly extracted with 100 mL aliquots of 2-butanone. The organic extracts were dried over magnesium sulfate, filtered, and concentrated under reduced pressure to yield 3.42 g of a reddish syrup which contained 36.9% w/w % sucralose (31.1% yield over two steps). The aqueous phase contained additional sucralose which can be recovered by repeated 2-butanone extraction.

What is claimed is:

1. A process for producing sucralose from a feed mixture of (a) 6-O-acyl-4,1',6'-trichloro-4,1',6'-trideoxygalactosucrose, (b) salt including alkali metal or alkaline earth metal chloride, (c) water, and (d) other chlorinated sucrose by-products, in a reaction medium comprising a tertiary amide, wherein said process comprises:

(i) deacylating the 6-O-acyl-4,1',6'-trichloro-4,1',6'-trideoxygalactosucrose by raising the pH of the aqueous solution of (a), (b), (c) and (d) to about 11 (±1) at a temperature and for a period of time sufficient to effect said deacylation, to produce an aqueous solution comprising sucralose, salt including alkali metal or alkaline earth metal chloride, and other chlorinated sucrose by-products, in a reaction medium comprising a tertiary amide;

(ii) removing said tertiary amide; and (iii) recovering sucralose from the product of step (ii).

2. The process of claim 1 wherein step (ii) is carried out by steam stripping.

3. The process of claim 2 wherein the tertiary amide is N,N-dimethylformamide.

4. The process of claim 3 wherein the 6-O-acyl-4,1',6'-trichloro-4,1',6'-trideoxygalactosucrose is 6-O-acetyl-4,1',6'-trichloro-4,1',6'-trideoxygalactosucrose or 6-O-benzoyl-4,1',6'-trichloro-4,1',6'-trideoxygalactosucrose.

5. The process of claim 4 wherein the step of extracting sucralose from the product of step (iii) is carried out by a batch, continuous, or continuous counter-current extraction.

6. The process of claim 5 wherein the sucralose is further purified by crystallization.

7. The process if claim 6 wherein the crystallization is carried out from water or ethyl acetate.

8. A process for producing sucralose from a feed mixture of (a) 6-O-acyl-4,1',6'-trichloro-4,1',6'-trideoxygalactosucrose, (b) salt including alkali metal or alkaline earth metal chloride, (c) water, and (d) other chlorinated sucrose by-products, in a reaction medium comprising a tertiary amide, wherein said process comprises:

(i) removing said tertiary amide to produce an aqueous solution of (a), (b) and (d) from which a major proportion of the tertiary amide in said feed mixture has been removed;

(ii) deacylating the 6-O-acyl-4,1',6'-trichloro-4,1',6'-trideoxygalactosucrose by raising the pH of the aqueous solution product of step (i) to a pH of at least about 11 (±) at a temperature and for a period of time sufficient to effect said deacylation, to produce an aqueous solution comprising sucralose, salt including alkali metal or alkaline earth metal chloride, and other chlorinated sucrose by-products; and (iii) recovering sucralose from the product of step (ii).

9. The process of claim 8 wherein the 6-O-acyl-4,1',6'-trichloro-4,1',6'-trideoxygalactosucrose is 6-O-acetyl-4,1',6'-trichloro-4,1',6'-trideoxygalactosucrose or 6-O-benzoyl-4,1',6'-trichloro-4,1',6'-trideoxygalactosucrose.

10. The process of claim 9 wherein step (iii) is carried out by extracting sucralose from the product of step (ii) by an organic solvent, followed by crystallization of sucralose from said organic solvent.

11. The process of claim 10 wherein said organic solvent is ethyl acetate.

12. The process of claim 9 wherein step (iii) is carried out by extracting sucralose from the product of step (ii) by an organic solvent, followed by crystallization of sucralose from water.

13. The process of claim 9 wherein the tertiary amide is N,N-dimethylformamide.

14. The process of claim 13 wherein the removal of the tertiary amide in Step (i) is effected by steam distillation.

15. The process of claim 11 wherein the step of extracting sucralose from the product of step (ii) is carried out by a batch, continuous, or continuous counter-current extraction.

\* \* \* \* \*

UNITED STATES PATENT AND TRADEMARK OFFICE
CERTIFICATE OF CORRECTION

PATENT NO. : 5,498,709
APPLICATION NO. : 08/443710
DATED : March 12, 1996
INVENTOR(S) : Navia et al.

Page 1 of 1

It is certified that error appears in the above-identified patent and that said Letters Patent is hereby corrected as shown below:

Column 2, line 55, "["TGS-6-ester"]" should read --["TGS-6-ester"]--.

Column 6, line 12, "sucralose-6acetate" should read --sucralose-6-acetate--.

In claim 8, column 12, line 16, "11 (+/-)" should read --11 (+/-1)--.

Signed and Sealed this

Ninth Day of January, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,498,709 | Page 1 of 1 |
| APPLICATION NO. | : 08/448710 | |
| DATED | : March 12, 1996 | |
| INVENTOR(S) | : Navia et al. | |

It is certified that error appears in the above-identified patent and that said Letters Patent is hereby corrected as shown below:

Column 2, line 55, "["TGS-6-ester"]" should read --["TGS-6-ester"]--.

Column 6, line 12, "sucralose-6acetate" should read --sucralose-6-acetate--.

In claim 8, column 12, line 16, "11 (+/-)" should read --11 (+/-1)--.

This certificate supersedes Certificate of Correction issued January 9, 2007.

Signed and Sealed this

Sixth Day of February, 2007

JON W. DUDAS
*Director of the United States Patent and Trademark Office*